United States Patent [19]
Höfliger et al.

[11] Patent Number: 5,103,087
[45] Date of Patent: Apr. 7, 1992

[54] PROCESS FOR KEEPING DUSTFREE AN APPARATUS FOR DETECTING IMPURITY PARTICLES

[75] Inventors: Harro Höfliger, Allmersbach im Tal; Gerhard Barth, Karlsruhe, both of Fed. Rep. of Germany

[73] Assignee: Harro Hofliger Verpackungsmaschinen GmbH, Allmersbach im Tal, Fed. Rep. of Germany

[21] Appl. No.: 501,543

[22] Filed: Mar. 30, 1990

[30] Foreign Application Priority Data

Apr. 6, 1989 [DE] Fed. Rep. of Germany ....... 3911112

[51] Int. Cl.⁵ .................................................. G01N 9/04
[52] U.S. Cl. ................................. 250/223 B; 356/240
[58] Field of Search ............... 250/223 R, 223 B, 573, 250/575; 356/337, 436–440, 239, 240, 426, 427; 209/586–588

[56] References Cited

U.S. PATENT DOCUMENTS

| | | | |
|---|---|---|---|
| 3,953,136 | 4/1976 | Hach | 250/576 |
| 4,172,524 | 10/1979 | Holm et al. | 356/427 |
| 4,349,112 | 9/1982 | Wilkes | 250/223 R |
| 4,385,233 | 5/1983 | Lovalenti | 250/223 B |
| 4,902,137 | 2/1990 | Krieg et al. | 356/427 |
| 4,951,825 | 8/1990 | Hawkin et al. | 209/586 |

Primary Examiner—David C. Nelms
Assistant Examiner—S. Allen
Attorney, Agent, or Firm—Antonelli, Terry, Stout & Kraus

[57] ABSTRACT

A process and apparatus for detecting impurity particles in fluids, particularly in infusion solutions contained in bottles, with the apparatus including illuminating and etecting device for defining an optical path through which a fluid is conveyed along a fluid conveying path. To increase reliability of detection, pure air is blow from the optical path into a fluid conveying channel thereby ensuring freedom from dust. The conveying channel of the fluid in a vicinity of the illuminating and detecting device, in a direction of the optical path, has an opening, and a blower having a filter is located on the other side of the opening, as viewed in a direction of the conveying path.

5 Claims, 1 Drawing Sheet

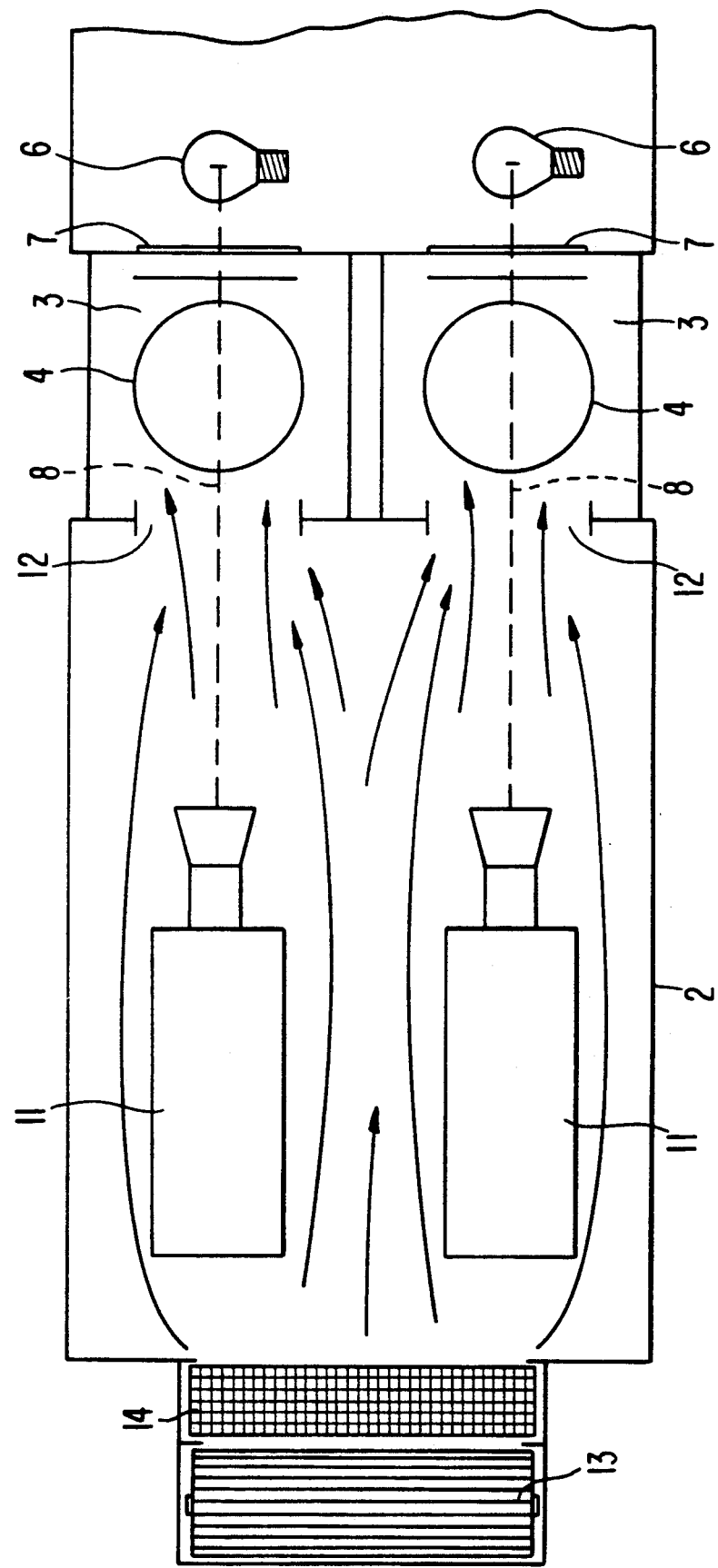

PROCESS FOR KEEPING DUSTFREE AN APPARATUS FOR DETECTING IMPURITY PARTICLES

FIELD OF THE INVENTION

The invention relates to a process for keeping dustfree the optical path of an apparatus for detecting impurity particles in fluids, particularly in infusion solutions or the like in bottles, with an illuminating and a detecting device, through whose optical path is passed the fluid, as well as to an apparatus for performing the process.

BACKGROUND OF THE INVENTION

In the case of apparatuses for detecting impurity particles in fluids and in particular microscopic impurity particles, it has been found that the measured result can be falsified by dust particles from the ambient air travelling in the optical path, because they can give rise to an error signal, although the bottle or fluid being investigated is itself fault-free. Such an apparatus is fundamentally known from DE-OS 37 03 306, whose disclosure is made part of the subject matter of the present application and to which reference is made.

SUMMARY OF THE INVENTION

The aim underlying the present invention resides in providing a process and an apparatus preventing or eliminating disturbing influences of dust particles in the air surrounding the fluid under investigation, while increasing the detection reliability of an apparatus for detecting impurity particles in fluids.

The invention provides a process for solving this problem, in which pure air is blown from the optical path into the fluid delivery or conveying path. An apparatus according to the invention is characterized in that the fluid delivery or conveying channel has an opening in the direction of the optical path in the vicinity of the illuminating and detecting device and that, seen from the conveying path, a blower provided with a filter is arranged on the other side of the opening.

As in the case of closed rooms to be kept clean, it would be obvious to suction the air out of these and said air could be replaced as a result of the vacuum occurring by air flowing in through a filter. However, it has been found that it is not possible to realize such a construction in apparatuses for detecting impurity particles in fluids, or at least that no optimum dustproof effect is obtained, particularly in the detection beam through which the fluid is passed. The procedure adopted by the invention is that pure air is blown from the optical path into the conveying or delivery path of the fluid to be supplied. This reliably excludes dust flowing into and through the conveying path to the optical path through the openings necessarily provided at the inlet and outlet for the fluid conveying path and through which dust could enter. The invention prevents the dust from entering the fluid conveying path or, to the extent that any dust penetrates or is conveyed in by adhesion to the bottles containing the fluid, it is torn away by the pure air flow and passed from the optical path to the inlet and outlet of the fluid into or out of the conveying path thereof. According to a preferred construction the pure air is blown into the conveying path both in the supply and carrying away direction. By suitable guidance measures, such as guide plates or the like, a larger proportion of the pure air can be blown counter to the conveying direction, because there is a greater risk of dust penetrating at the fluid inlet point than in the outlet area. According to another construction the pure air is blown into the conveying path from the observation side of the illuminating and detection device. According to another construction the pure air is blown from an area behind the detection device counter to the optical path of the illuminating and detection device towards the conveying path. According to a further development of the inventive apparatus, the latter is characterized in that the blower with filter is positioned relative to the conveying channel on the other side of the detection devices.

BRIEF DESCRIPTION OF THE DRAWINGS

Further advantages and features of the invention can be gathered from the claims and the following description of an embodiment of the invention with reference to the drawing, wherein The single FIGURE is a schematic cross-sectional view of an apparatus for detecting impurity particles constructed in accordance with the present invention.

DETAILED DESCRIPTION

The inventive apparatus is an apparatus for detecting impurity particles, particularly microscopic impurity particles in fluids, particularly infusion solutions or the like contained in bottles and as is in particular known from EP-A-277 629 and corresponding U.S. Pat. No. 4,902,137. The disclosure of the latter specification forms part of the present application. The inventive apparatus 1 has a casing 2 in which there are two vertically directed conveying or delivery paths or channels 3 for infusion bottles 4 to be delivered or conveyed therein and whose content can be investigated. In the represented drawing to the right of the conveying paths 3 there are light sources 6, which are separated from paths 3 by a transparent disk 7. In addition, between light source 6 and bottle 4 is provided a polarizing filter and a diaphragm or frame, which in particular blocks out the central area of the bottle on optical axis 8 from the light beam of lamp 6. A camera 11 is located diametrically opposite lamp 6 relative to bottle 4. The casing 2 has a connecting opening 12 from the conveying channel 3 to camera 11. On the side of camera 11 remote from the conveying paths 3, a blower 13 is provided on casing 1 with a filter 14 located between the blower and the interior of casing 2. The conveying paths or channels 3 for the infusion bottles 4 are obviously open at their inlet and outlet, so that the bottles 4 can be conveyed into the conveying channels 3. From the area surrounding the apparatus 1, blower 13 suctions air and forces it through the filter 14 into the interior of casing 2, with the air being purified by the interchangeable filter 14. The air conveyed into the interior of casing 2 on the back of camera 11 flows through the openings 12 into the conveying channels 3 and along the latter in the conveying direction and counter to the conveying direction of the bottles 2 to the bottle inlet and outlet point, where the air blown into the casing 2 passes out of the latter again. Thus, the entire optical path from the camera 11 to the bottles 4 and the latter has filtered, purified air flowing around the same, so that no dust particles can enter via the inlet and outlet for the bottles, or if such particles are conveyed into channels 3 adhering to the bottles are removed from the latter by the air flow and are scavenged out of the channels 3 again. As a result of the inventive arrangement there is a complete scavenging of the casing interior and therefore the optical path is kept completely free, as are the surfaces of the bottles 4 to be investigated in the investigation area. Therefore dust particles cannot lead to a falsification of the measured result. As the optical path is kept free from dust particles, the inventive testing arrangement in the represented form only detects the impurity particles in the bottles. Such a cleaning of the optical path is particularly important if microscopic impurity particles of a few dozen micrometers located in the bottles 4 are to be reliably detected, so that the bottles can be eliminated.

We claim:

1. Process for keeping an optical path of an apparatus for detecting impurities in infusion solutions contained in bottles dustfree, the method comprising the steps of passing a fluid through an optical path defined between an illuminating means and a detecting means, and blowing purified air along the optical path into a conveying path of bottles from a side of the detecting means.

2. Process for keeping an optical path of an apparatus for detecting impurities in infusion solutions contained in bottles dustfree, the method comprising the steps of passing a fluid through an optical path defined between an illuminating means and a detecting means, and blowing purified air along the optical path into a conveying path from an area behind the detecting means in a direction toward the illuminating means.

3. Process according to one of claims 1 or 2, wherein said purified air is blown into the conveying path in a supply direction and a discharge direction of the bottles along the conveying path.

4. Apparatus for detecting impurity particles in infusion fluids in bottles, the apparatus comprising an illuminating means for emitting a light beam, a detecting means for detecting the emitted light beam, said illuminating means and said detecting means being arranged so as to define an optical path, conveying channel means arranged so as to convey the bottles through the apparatus, an opening means provided in said conveying channel means for enabling the emitted light to reach the detector means after passing through the fluid in said bottles, and a blower means provided with a filter means for supplying purified air, said blower means being arranged on a side of the detecting means and being adapted to blow purified air into the conveying channel means through said opening means.

5. Apparatus according to claim 4, wherein said blower means with said filter means is arranged on a side of the detecting means opposite a side thereof facing said conveying channel means.

* * * * *